(12) United States Patent
Thakur et al.

(10) Patent No.: US 10,208,306 B2
(45) Date of Patent: Feb. 19, 2019

(54) COMPOSITIONS AND METHODS TO PROMOTE BONE FORMATION

(71) Applicant: THE RESEARCH FOUNDATION FOR THE STATE UNIVERSITY OF NEW YORK, Albany, NY (US)

(72) Inventors: Nikhil A. Thakur, East Syracuse, NY (US); Bryan S. Margulies, Syracuse, NY (US)

(73) Assignee: The Research Foundation for the State University of New York, Albany, NY (US)

( * ) Notice: Subject to any disclaimer, the term of this patent is extended or adjusted under 35 U.S.C. 154(b) by 0 days.

(21) Appl. No.: 14/723,894

(22) Filed: May 28, 2015

(65) Prior Publication Data

US 2015/0344882 A1   Dec. 3, 2015

Related U.S. Application Data

(60) Provisional application No. 62/005,359, filed on May 30, 2014.

(51) Int. Cl.
  *A61K 45/06*   (2006.01)
  *A61K 31/485*   (2006.01)
  *C12N 15/113*   (2010.01)

(52) U.S. Cl.
  CPC .......... *C12N 15/113* (2013.01); *A61K 31/485* (2013.01); *A61K 45/06* (2013.01); *C12N 15/1138* (2013.01); *C12N 2310/14* (2013.01); *C12N 2310/531* (2013.01)

(58) Field of Classification Search
  USPC ...................................................... 424/400
  See application file for complete search history.

(56) References Cited

U.S. PATENT DOCUMENTS

| | | |
|---|---|---|
| 5,882,944 A | 3/1999 | Sadee |
| 6,007,986 A | 12/1999 | Sadee |
| 6,270,979 B1 | 8/2001 | Sadee |
| 6,713,488 B2 | 3/2004 | Sadee et al. |
| 8,518,962 B2 | 8/2013 | Moss et al. |
| 2007/0197573 A1 | 8/2007 | Sadee et al. |
| 2011/0165218 A1 | 7/2011 | Cool et al. |
| 2012/0100114 A1 | 4/2012 | Gregory et al. |

FOREIGN PATENT DOCUMENTS

| | | |
|---|---|---|
| WO | WO 97/39767 A1 | 10/1997 |
| WO | WO 2006/044334 A2 | 4/2006 |

OTHER PUBLICATIONS

Yaffe (Journal of Periodontology, Jul. 2003, vol. 74, No. 7, pp. 1038-1042).*

Kim D.H. et al., "Strategies for Silencing Human Disease Using RNA Interference", Nature Reviews—Genetics 8(3):173-184 (Mar. 2007).
Petrizzi L. et al., "Preliminary Study on the Effect of Parenteral Naloxone, Alone and in Association With Calcium Gluconate, on Bone Healing in an Ovine "Drill Hole" Model System", BMC Musculoskeletal Disorders 8:43:1-9 (2007).
Rose F.R.A.J. et al., "Delivery System for Bone Growth Factors—the New Players in Skeletal Regeneration", Journal of Pharmacy and Pharmacology 56:415-427 (2004).
International Search Report and Written Opinion dated Sep. 1, 2015 received from Application No. PCT/US15/32820.
Caplan A.I. et al., "PDGF in Bone Formation and Regeneration: New Insights into a Novel Mechanism Involving MSCs", Journal of Orthopaedic Research 29:1795-1803 (Dec. 2011).
Cheng F. et al., "The OGF-OGFr Axis Utilizes the p16INK4a and p21WAF1/CIP1 Pathways to Restrict Normal Cell Proliferation", Molecular Biology of the Cell 20:319-327 (Jan. 1, 2009).
Elhassan A.M. et al., "Methionine-Enkephalin in Bone and Joint Tissues", Journal of Bone and Mineral Research 13 (1):88-95 (1998).
Kuis W. et al., "Differential Processing of Proenkephalin-A by Human Peripheral Blood Monocytes and T Lymphocytes", J. Clin. Invest. 88:817-824 (Sep. 1991).
Liskov A.V. et al., "Effect of Naloxone Hydrochloride on Osteogenesis in Chick Embryos", Bulletin of Experimental Biology and Medicine 139(3):331-333 (2005).
March J., Advanced Organic Chemistry—Reactions, Mechanisms, and Structure, Third Edition, pp. 237-250 (1985).
Perez-Castrillon J. et al., "Expression of Opioid Receptors in Osteoblast-Like MG-63 Cells, and Effects of Different Opioid Agonists on Alkaline Phosphatase and Osteocalcin Secretion by These Cells", Neuroendocrinology 72:187-194 (2000).
Rosen H. et al., "Perspective—The Enkephalinergic Osteoblast", Journal of Bone and Mineral Research 13(10):1515-1520 (1998).
Rosen H. et al., "Proenkephalin A in Bone-Derived Cells", Proc. Natl. Acad. Sci. USA 88:3705-3709 (May 1991).
Valdes M. et al., "Long Acting Opioid Antagonists Stimulate Mesenchymal Stem Cells Osteoblastic/Chondroblastic Differentiation", Poster No. 1732, ORS 2011 Annual Meeting.
Valdes M. et al., "Dose-Dependent Naloxone Exposure Stimulates Osteoblastic Differentiation in Negatively Immunodepleted Mesenchymal Stem Cells", Poster No. 1328, 55th Annual Meeting of the Orthopaedic Research Society (2010).
Akhavan, A. et al., "Topical Acne Drugs: Review of Clinical Properties, Systemic Exposure, and Safety", Am J Clin Dermatol, (2003), vol. 4, No. 7, pp. 473-492.
Baamonde, A. et al., "Effects of local administration of selective μ-, δ-and κ-opioid receptor agonists on osteosarcoma-induced hyperalgesia", Naunyn-Schmiedeberg's Arch Pharmacol, (2005), 372: pp. 213-219.

(Continued)

*Primary Examiner* — Devang K Thakor
(74) *Attorney, Agent, or Firm* — Foley & Lardner LLP

(57) ABSTRACT

This disclosure relates to methods for promoting bone formation or reducing bone destruction. This disclosure also relates to methods for promoting the recruitment of mesenchymal stem cells (MSC) to a local site of injury or surgical intervention in bone to promote healing. In addition, this disclosure relates to methods for reducing or preventing mineral formation or bone growth, or reducing bone mass. The methods disclosed herein are useful for treating conditions such as osteoradionecrosis.

14 Claims, 8 Drawing Sheets
Specification includes a Sequence Listing.

(56) References Cited

OTHER PUBLICATIONS

Goblirsch, M.J. et al., "Advances in Understanding Bone Cancer Pain", Journal of Cellular Biochemistry, (2005), vol. 96, pp. 682-688.
Goblirsch, M.J. et al., "Biology of Bone Cancer Pain", Clin Cancer Res, (2006), 12 (20 Suppl), 6 pages.
Levine, J.D. et al., "The narcotic antagonist naloxone enhances clinical pain", Nature, (Apr. 1978), vol. 272, 2 pages.
McDougall, J.J. et al., "Peripheral analgesia: Hitting pain where it hurts", Biochimica et Biophysica, (2011), pp. 459-467.
Newport, K. et al., "Topical Cocaine for Relief of Mucosal Pain", Journal of Pain & Palliative Care Pharmacotherapy, (2010), vol. 24, pp. 149-151.
Smith, H., "Aspirin-Inspired Analgesia: Old Drug, New Mechanism, Sans Cox?" Pain Physician, (2012), vol. 15, pp. E359-E361.
Steg, G., "Agents antiplaquettaires et atherothrombose", Bull. Acad. Natle Med., (2013), vol. 197, No. 2, pp. 375-388, (with English Summary).
Stein, C. et al., "Peripheral Opioid Receptors Mediating Antinociception in Inflammation. Evidence for Involvement of Mu, Delta and Kappa Receptors", The Journal of Pharmacology and Experimental Therapeutics, (1989), vol. 248, No. 3, pp. 1269-1275.
Vermeulen, H. et al., "Benefit and harm of iodine in wound care: a systematic review", Journal of Hospital Infection, (2010), vol. 76, pp. 191-199.
Yoshida, S. et al., "Guidelines for Iodine Prophylaxis as a Protective Measure: information for Physicians", JMAJ, (May/Jun. 2014), vol. 57, No. 3, pp. 113-123.
Zimmermann, M.B. et al., "Iodine Deficiency", Endocrine Reviews, (Jun. 2009), vol. 30, No. 4, pp. 376-408.
Supplementary European Search Report dated Apr. 21, 2017 issued in Corresponding European Patent Application No. EP 15799544.0.
European Office Action dated Feb. 15, 2018 issued in EP 15 799 544.0.

* cited by examiner

COMPOSITIONS AND METHODS TO PROMOTE BONE FORMATION

CROSS REFERENCE TO RELATED APPLICATION

This application claims the benefit of priority from U.S. Provisional Application No. 62/005,359, filed May 30, 2014, the entire contents of which are incorporated herein by reference.

INCORPORATION BY REFERENCE OF SEQUENCE LISTING

The Sequence Listing in an ASCII text file, named 30878_SEQ.txt of 2 KB, created May 11, 2015, and submitted to the United States Patent and Trademark Office via EFS-Web, is incorporated herein by reference.

BACKGROUND ART

Bone formation and degradation are tightly regulated by growth factor signaling between osteoblasts that are responsible for bone formation and osteoclasts that are responsible for bone re-absorption. Coupling bone formation by osteoblasts with degradation by osteoclasts has recently become a topic of intense study; with the list of growth factors identified as coupling factors expanding. Coupling bone formation with bone re-absorption requires the recruitment of osteoblasts and osteoclasts in parallel with the recruitment of their respective progenitor cells. Osteoblasts derive from mesenchymal stem cell (MSC) while osteoclasts derive from monocytes that are a part of the myeloid-lineage; however, it remains unknown how MSC or monocytes migrate from their niche in the bone marrow to sites of new bone formation. The current understanding of the spatial and temporal regulation of osteogenesis proposes that MSC migrate from their bone marrow niche to the endosteal surface; where the MSC differentiate into osteoblasts that produce new bone. In parallel, monocytes also migrate from their bone marrow niche to the endosteal surface; where they subsequently differentiate into osteoclasts that re-absorb bone. Growth factors known to regulate bone formation include TGFβ-, BMP- and the canonical Wnt-ligands. Osteoclast formation from monocyte precursors and bone re-absorption are regulated through the expression of MSCF, OPG and RANK-ligand. In parallel, osteoclast activity is also regulated by the expression of the TGFβ-, BMP- and the non-canonical Wnt-ligands. However, many developmental growth factors involved in tissue patterning, including TGFβ-, BMP- and the Wnt-ligands, promote bone formation and re-absorption. The maintenance of healthy bone requires constant remodeling, in which bone is made and destroyed continuously.

The introduction of an implant into bone results in a biochemical cascade that drives the pro-inflammatory response that is partially mediated by macrophage activity, which are derived from the myeloid lineage and can contribute to the degradation of bone or an implant material. Currently implants and implant materials are chosen to minimize the macrophage response while being optimally osteo-conductive and promoting maximum bone-implant integration. Alternatively, the introduction of autograft with an implant or the use of devitalized bone tissue graft (autograft) has been employed in concert with the material properties of an implant as a means of increasing osteo-integration; however, these approaches have often been problematic. Ideally, materials could be designed to be both self-organizing and self-assembling.

Generating bone as an adjuvant therapeutic approach employed during orthopedic trauma procedures or during routine spine fusion procedures represents a continuing challenge in orthopedic surgery. Specifically, these adjuvant bone-generating therapies seek to increase the growth of healthy bone at the site of surgical intervention in parallel with decreasing the healing time for bone. In the last several decades a number of attempts have been made to use various growth factors with osteogenic potential, including Bone Morphogenci Protein (BMP). Unfortunately, BMP based therapies intended to generate bone also carry a risk for tumorigenesis in patients, particularly those who may be undergoing X-radiation therapy or possess nascent undetected tumor. Further, BMP based therapies cannot be used in patients with active tumor, which is particularly unfortunate since these patients would benefit significantly from therapies that increase bone formation during surgical intervention.

Impaired fracture healing continues to present a significant challenge in orthopedic surgery and bone healing. Fracture non-union rates as high as 5-20% have been reported. The morbidity and cost associated with the treatment of patients developing non-unions can be substantial. Approximately 10% of the 6.2-million fractures encountered each year have difficulty healing. Various options exist to help accelerate bone healing, with unproven efficacy. Iliac crest bone graft is still considered to be the gold standard but has significant issues related to harvest site co-morbidity. Growth factor based therapies that include platelet-derived growth factor (PDGF), fibroblast growth factor (FGF) and parathyroid hormone (PTH) has shown initial success in cell culture studies; however, their efficacy remains unproven in clinical application. An additional option, such as bone morphogenic protein-2 (BMP2) and BMP7, has been shown to have success in accelerating fracture healing with diaphyseal fractures. However, there are risks associated with the use of BMP that include increased infection, increased risk of tumor growth, and an increased risk of local osteolysis. Many of the risks associated with treatments that include BMP also preclude the use of BMP for patients with other pathologies.

The therapeutic ability to increase bone formation, as an adjuvant during orthopedic surgery, while not increasing the potential for tumor growth is currently a limitation of commercially available biologics, when treating complex orthopedic problems such as spine fusion, fracture healing and the management of fracture non-unions.

In the field of orthopedic trauma, particularly with open fractures with large defects and non-unions; autogenous/allogenic bone grafts are the primary treatment options. However, autogenous harvested bone graft, used as the gold standard to achieve bone formation, has risks of infection and donor site pain. Other allogenic bone graft substitutes have shown poor healing when used singularly. The same limitations exist for spine surgeries when these graft options are used to achieve fusions.

Cortical and cancellous bone derived from cadaveric sources serves to fill space and is primarily osteo-conductive without significant osteo-inductive potential. Hence, biologics such as PDGF, VEGF and BMP are used to increase rates of healing or spine fusion, and their application adds to the cost of treatment. However, these biologic therapies stimulate proliferation during development in a range of cell phenotypes, which presents an inherent and unacceptable tumor risk.

De-mineralized bone matrix and calcium phosphate substitutes have not shown high efficacy at accelerated bone healing and also have significant cost associated with them due to production costs.

Recombinant BMP2 (rhBMP2) is an implant commercially developed by Medtronic known as INFUSE that is distributed in small (4.2-mg of BMP2 with 2× collagen sponges for a 15-mg/cm$^3$ implant), medium (8.4-mg of BMP2 with 4× collagen sponges for a 15-mg/cm$^3$ implant), large (12-mg of BMP2 with 6× collagen sponges for a 15-mg/cm$^3$ implant) and large-II (12-mg of BMP2 with 1× collagen sponge for a 15-mg/cm$^3$ implant). All sizes of the INFUSE implant are approved for spine and maxillofacial applications while only the large-II implant is approved for fracture. An INFUSE implant is administered by reconstituting the powdered BMP2 with sterile saline and then adding the BMP2-saline solution to the collagen sponge; after which the implant is delivered locally during surgical intervention.

Recombinant BMP7 (rhBMP7 or OP1) is an implant commercially developed by Stryker and now owned by Olympus known as OP1. OP1 implants are distributed as OP1-putty (20-mL vial containing powdered bovine cartilage and 3.3-mg of BMP7) or OP1-implant (1-g of powdered bovine cartilage and 3.3-mg of BMP7). The OP1-putty is approved for spine fusion surgeries while the OP1-implant is approved for treating fractures and fracture non-union surgery. The OP1-putty or the OP1-implant is administered by, reconstituting the powdered BMP7 with sterile saline first, and then adding the BMP7-saline solution to the collagen implant; after which the implant is delivered locally during surgical intervention.

The opioid growth factor-receptor (OGFR or ζ-opioid receptor) is a non-canonical, peri-nuclear opioid-receptor that does not share structural homology with the canonical μ-, κ- and δ-opioid-receptors (OPRM, OPRK and OPRD, respectively) and binds the native opioid-ligands less efficiently than the canonical opioid receptors. The opioid growth factor (OGF or met-5 enkephalin; met5) is the native ligand for the OGFR. Met5 is derived from the pro-hormone pro-enkephalin (PENK) and to a lesser extent pro-opiomelanocortin (POMC), which are first reduced by prohormone convertase (PCSK1 and PCSK2) and then carboxypeptidase E or D (CPE or CPD; enkephalin convertase) to form five copies of met5-enkephalin. Previous work identified met5 expression in osteoblasts and osteoprogenitors (Rosen et al., Proc Natl Acad Sci 88(9):3705-9, 1991; Rosen et al., J Bone Miner Res. 13(10):1515-20, 1998; Elhassan et al., J Bone and Miner Res., 13(1): 88-95, 1998; Cheng et al., Mol Biol Cell. 20(1):319-27, 2009). Additionally, Kuis et al. identified met5 in monocytes of the peripheral blood and spleen (Kuis et al., J Clin Invest. 88(3):817-24, 1991). Nevertheless, these investigators failed to identify a functional significance for OGFR-signaling in mesenchymal of myeloid lineages. Elhassan et al. (J Bone and Miner Res, 13(1): 88-95, 1998) discloses the presence of met5 in bone and joint tissues. However, there is no demonstrable link between met5 and bone formation.

SUMMARY OF THE DISCLOSURE

It has been identified herein that inhibition of opioid growth factor signaling, promotes bone formation and/or reduces bone destruction. Without intending to be bound by any particular theory, it is believed that inhibition of the opioid growth factor signaling through the opioid growth factor receptor (OGFR) is effective to promote bone formation and/or reduce bone destruction. It has been demonstrated herein that inhibition of opioid growth factor signaling promotes bone formation in an animal by locally administering an inhibitor of the opioid growth factor (OGFR) signaling pathway directly to the site where bone formation is desired. It has also been demonstrated that administration of an inhibitor of the opioid growth factor signaling pathway directly to the site where bone formation is desired is required to promote the differentiation of MSC to become osteoblasts and prevent the differentiation of monocytes into osteoclasts, which leads to the increase in mineralization, and the increase in bone formation at a site of bone injury or surgery.

Accordingly, the present invention is directed to a method for promoting bone formation or reducing bone destruction, by administering to an animal in need thereof, an amount of an antagonist of the opioid growth factor receptor effective to promote bone formation and/or reduce bone destruction directly to a site where bone formation is desired.

In one aspect, the OGFR antagonist employed in the present method blocks the binding of opioid growth factor to the OGFR.

In some embodiments, the OGFR antagonist that blocks the binding of opioid growth factor (met5) to OGFR is naloxone or a functional derivative thereof, naltrexone or a functional derivative thereof, or a combination thereof.

In other embodiments, OGFR antagonists are derived from oxymorphone and bind to the OGFR, which include: naloxone, naltrexone, nalorphine, naloxonazine, levallorphan, nalmefene, cyprodime, cyclorphan, cyclazocine, oxilorphan, LY113878, MR2266, diprenorphine, WIN 44,441-3, naltindole, or norbinaltorphimine.

In still other embodiments, OGFR antagonists are derived from trans-3,4-dimethyl-4-phenylpiperidine and bind to the OGFR, which include: LY99335, LY25506, LY117413, or LY255582.

In some embodiments, OGFR antagonists are derived from the met5-enkephalin or leu-enkephalin peptides, bind to the OGFR, and minimally include the following amino acid sequences as a means of targeting the OGFR: Tyr-Gly-Gly-Phe-Met (SEQ ID NO: 1) for those derived from met5-enkephalin or Tyr-Gly-Gly-Phe-Leu (SEQ ID NO: 2) for those derived from the leu-enkephalin.

In still other embodiments, OGFR antagonists are derived from the peptide antagonist ICI174864 (N,N-diallyl-Tyr-Aib-Aib-Phe-Leu-OH, SEQ ID NO: 3; Aib=aminoisobutytic acid) or somatostatin analog CTP (D-Phe-Cys-Tyr-D-Trp-Lys-Thr-Pen-Thr-NH$_2$, SEQ ID NO: 4).

In another aspect, the OGFR antagonist employed in the present methods is a molecule that disrupts the nuclear localization sequence found within OGFR: 251 QSALDYF-MFAVRCRHQRRQLVHFAWEHFRPRCKFVWGPQDKL-RRFKPSSL (SEQ ID NO: 5).

In still another aspect, the OGFR antagonist employed in the present methods is a small-hairpin (sh)-RNA or a small-interfering (si)-RNA directed against the OGFR gene and effective in disrupting OGFR gene expression.

In another aspect, this disclosure provides a method for promoting the recruitment of mesenchymal stem cells (MSC) to a local site of injury or surgical intervention in bone to promote healing while inhibiting osteoclast driven bone degradation (or re-absorption). The method is based on administration of an amount of an OGFR antagonist to promote bone formation while inhibiting bone degradation. The injury can be, e.g., bone fracture or a surgical intervention. In some embodiments, the OGFR antagonist is administered locally to the site of injury or site of surgical intervention.

DETAILED DESCRIPTION

Figures 1A, 1B, 1C:
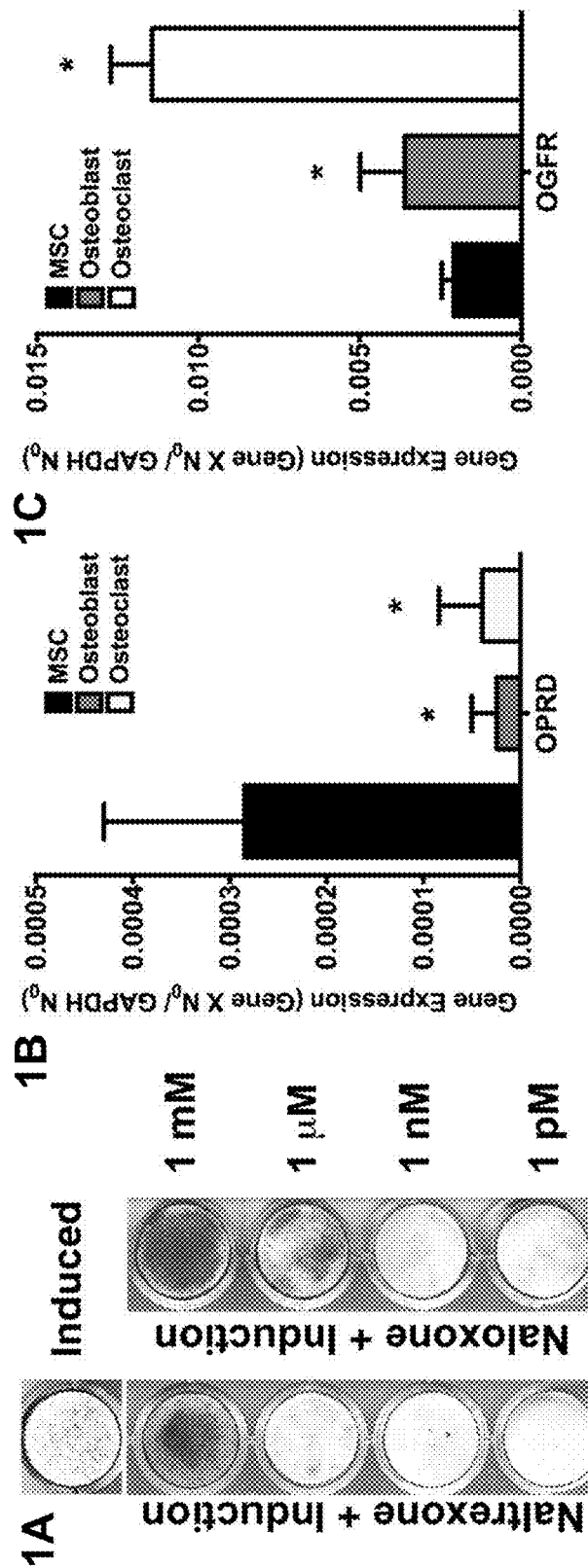
FIGS. 1A-1I: (A) The addition of naloxone between 1-µM and 1-mM with osteoinduction media substantially increased mineral accumulation (red staining) in MSC cultures induced to become osteoblasts. The addition of naltrexone between 1-µm and 1-mm with osteoinduction media also increased mineral, but to a lesser extent than naloxone. (B) The delta opioid receptor (OPRD) gene expression decreased substantially in osteoblasts (*=p<0.001) and osteoclasts (*=p<0.0084) while opioid growth factor receptor (OGFR) gene expression (C) increased significantly in osteoblasts (*=p<0.02) and osteoclasts (*=p<0.0001). (D) The OGFR-ligand, met5-enkephalin (met5), is derived from a larger precursor protein known as pro-enkaphalin (PENK). The addition of 5- or 50-µM of met5 had no effect on mineral formation in culture. (E) Importantly, adding 5-µM met5 (PENK) to osteoinduction media had no effect on mineral accumulation while 50-µm met5 decreased mineral accumulation slightly. However, when 1-mM of naloxone was added with 5-µM or 50-µM met5 and osteoinduction media, naloxone treatment was able to abrogate the anti-osteogenic effects of met5. (F) The addition of osteoinduction media resulted in mineral formation relative to control cultures. BMP2 increased mineral formation relative to controls while a single treatment (1× dose) with naloxone (1-mM) and two treatments (2×-dose) with naloxone increased mineral formation (red staining). Treatment with naloxone at each media change (continuous dose) suppressed mineral formation. (G) The addition of naloxone to MSC cultures decreased cell number at 72- and 120-hours (*=p<0.017). (H) The addition of naloxone to monocyte cultures also reduced cell number significantly (*=p<0.0001). (I) Monocytes cultured to become osteoclasts were unaffected by treatment with met5 relative to control osteoclast cultures (TRAP staining is purple). The addition of 1-µM of naloxone or 1-µM naltrexone did not significantly reduce osteoclast number while the addition of 1-mM of naloxone or 1-mM naltrexone reduced osteoclast number substantially.

It has been demonstrated herein that naloxone or naltrexone increases bone formation while decreasing osteoclast number. Increased bone formation is supported by mineral formation observed in culture and bone formation measured using micro-CT following a surgically induced unicortical defect with or without a bovine collagen carrier, or following fusion the posterolateral vertebral processes using a bovine collagen carrier. The surgical model resulted in an injury containing abundant albumin; which can sequester naloxone and naltrexone thereby supporting an extended availability of these OGFR antagonists.

In one aspect, the invention provides a method for promoting bone formation and/or reducing bone degradation. The method includes administering an amount of an OGFR antagonist to a local site of injury or surgical intervention in bone.

As used herein, a "surgical intervention" includes a surgical procedure to repair a fracture, a surgical procedure used to fuse vertebral bones (e.g. spine fusion), or a surgical procedure that includes, for example, integration of an implant during total joint arthroplasty, bone screws used during fracture repair, bone screws used to anchor tendons or ligaments, or any orthopedic hardware designed to mechanically stabilize the orthopedic surgical site.

OGFR Antagonist

By "OGFR antagonist" is meant any molecule that inhibits, suppresses or causes the cessation of at least one OGFR-mediated biological activity.

In some embodiments, an OGFR antagonist is an OGFR binding antagonist, namely, a molecule that, interferes with, blocks or otherwise prevents the interaction or binding of the met5-ligand (OGF) to the OGFR. An OGFR binding antagonist can function in two ways: First, the OGFR antagonist can compete with the met5-ligand for binding to the OGFR on the surface of the nuclear membrane, thereby interfering with, blocking or otherwise preventing the binding of the met5-ligand to the OGFR, without triggering the downstream signaling that would otherwise be induced by the binding of the met5-ligand to the OGFR. Alternatively, an OGFR binding antagonist can bind to or sequester PENK or the met5-ligand with sufficient affinity and specificity to substantially interfere with, block or otherwise prevent binding of met5-ligand to the OGFR, thereby inhibiting, suppressing or causing the cessation of at least one OGFR-mediated biological activity. Generally speaking, OGFR binding antagonists can be large molecules (e.g., antibodies) or small molecules (e.g., compounds of a molecular weight of less than 15-kD, 12-kD, 10-kD or even 8-kD), and can be a polypeptide, nucleic acid, or a synthetic small molecule compound. OGFR binding antagonists can be identified with any in vitro assay readily selected by one of skill in the art. For example, OGFR antagonists can be identified using the methods described in U.S. Pat. No. 5,882,944, U.S. Pat. No. 6,007,986, or U.S. Pat. No. 6,270,979.

In one embodiment, the OGFR binding antagonist is naloxone or a functional derivative thereof, naltrexone or a functional derivative thereof, or a combination thereof.

As used herein, a "functional derivative" refers to a derivative or analog that is structurally and functionally analogous to the originating molecule (e.g., maintains the function of naltrexone or naloxone as an OGFR antagonist). Naloxone and naltrexone analogs can be synthesized using standard synthetic procedures such as those described in March J., Advanced Organic Chemistry, 3rd Ed. (1985). Examples of naltrexone and naloxone functional derivatives include salt forms, e.g., naloxone hydrochloride dihydrate or naltrexone hydrochloride. Additional examples of naltrexone and naloxone functional derivatives suitable for use in the present methods include naltrexone and naloxone analogs disclosed in U.S. Patent Application Publication No. 2007/0197573 A1, U.S. Pat. No. 6,713,488, for example.

In another embodiment, an OGFR binding antagonist is derived from oxymorphone and binds to the OGFR, which includes naloxone, naltrexone, nalorphine, naloxonazine, levallorphan, nalmefene, cyprodime, cyclorphan, cyclazocine, oxilorphan, LY113878, MR2266, diprenorphine, WIN 44,441-3, naltindole, or norbinaltorphimine.

In still another embodiment, an OGFR binding antagonist is derived from trans-3,4-dimethyl-4-phenylpiperidine and binds to the OGFR, which includes LY99335, LY25506, LY117413, or LY255582.

In another embodiment, an OGFR binding antagonist is derived from the met5-enkephalin or leu-enkephalin peptides, binds to the OGFR, and minimally includes the following amino acid sequences as a means of targeting the OGFR: Tyr-Gly-Gly-Phe-Met (SEQ ID NO: 1) for those derived from met5-enkephalin or Tyr-Gly-Gly-Phe-Leu (SEQ ID NO:2) for those derived from the leu-enkephalin.

In still another embodiment, an OGFR binding antagonist is derived from the peptide antagonist ICI174864 (N,N-diallyl-Tyr-Aib-Aib-Phe-Leu-OH, SEQ ID NO: 3; Aib=aminoisobutytic acid) or somatostatin analog CTP (D-Phe-Cys-Tyr-D-Trp-Lys-Thr-Pen-Thr-NH$_2$, SEQ ID NO: 4).

In other embodiments, the OGFR antagonist, instead of being an OGFR binding antagonist, is a molecule that disrupts the nuclear localization sequence found within OGFR: 251 QSALDYFMFAVRCRHQRRQLVHFAWEH-FRPRCKFVWGPQDKLRRFKPSSL (SEQ ID NO: 5).

In still other embodiments, the OGFR antagonist employed in the present methods is a small-hairpin (sh)-RNA or a small-interfering (si)-RNA directed against the OGFR gene and effective in disrupting OGFR gene expression.

The OGFR antagonists described herein can be administered individually or in combination. Suitable combinations include, for example, naloxone and naltrexone; naloxone and/or naltrexone, in combination with another OGFR binding antagonist or another OGFR antagonist.

Combination of OGFR Antagonists with Other Active Agents

An OGFR antagonist described herein can be administered in combination with one or more other active agents that promote bone formation or growth via SMAD signaling, which can be synergistic to an OGFR antagonist. Examples of such active agents include, but are not limited to, a BMP molecule (e.g., BMP-2, BMP-4, BMP6 and BMP-7), which can regulate SMAD1/5/8 signaling. A TGFβ molecule that can expand the MSC pool that can then be regulated by an OGFR antagonist. TGFβ inhibitors, that include LY2109761, that reduce TGFβ signaling decrease inhibitor SMAD (SMAD6 and SMAD7) signaling and then antagonize BMP signaling and reduce bone formation. For example, a collagen implant can be infused with a desirable BMP molecule, a TGFβ molecule or a TGFβ inhibitor molecule and an OGFR antagonist for use in the present methods.

An OGFR antagonist described herein can be administered in combination with one or more other active agents that promote bone formation or growth. Examples of such active agents include, but are not limited to one or more growth factors, such as EGF, VEGF, PDGF, IGF, FGF, TGFα, and cytokines; cells such as mesenchymal stem cells, chondrocytes, and bone marrow cells. For example, a collagen implant can be infused with both a desirable growth factor such as a VEGF molecule and an OGFR antagonist for use in the present methods. An OGFR antagonist can also be administered in combination with a chemotherapeutic agent in treating a cancer patient to promote bone formation or growth in that patient.

Delivery Systems/Carriers

An OGFR antagonist described herein can be administered with or without a carrier locally to accelerate fracture repair or promote fusion of vertebral bone. In some embodiments, an OGFR antagonist is combined with or encapsulated within a carrier for administration.

Suitable carriers can be in bead, microsphere or nanoparticle form, and can be made of natural and/or synthetic biocompatible polymers. Examples of suitable biocompatible polymers include hyaluronic acid, collagen, tricalcium phosphate, chondroitin sulfate, polybutyrate, polylactide, polyglycolide, and lactide/glycolide copolymers, and mixtures or copolymers thereof. Suitable carriers also include non-polymer systems such as carboxylic acids, fatty acids, phospholipids, amino acids, lipids such as sterols, hydrogel release system; silastic system; peptide-based system; implants and the like.

In one embodiment, the carrier is a hygroscopic collagen based carrier (e.g., a collagen sponge, a collagen scaffold, a powdered collagen, or a collagen based gelatin hydrogel).

In another embodiment, the carrier is a hydrophilic hydrogel based carrier (e.g., poly lactic acid, poly glycolic acid), which allows an OGFR antagonist (e.g., naloxone or naltrexone or a functional derivative thereof) infused therein to be released over a period of time.

In still another embodiment, the carrier is albumin, a derivative or fragment of albumin that maintains the naloxone/morphine binding site located at the interface between the IA and IIA domains, and/or maintains the naloxone binding site around tryptophan (Trp)-214, that binds an OGFR antagonist such as naloxone or naltrexone or a functional derivative thereof and allows for a slow release of the OGFR antagonist.

In still another embodiment, methyl cellulose, and an insert gel, for example, that binds an OGFR antagonist such as naloxone or naltrexone or a functional derivative thereof and allows for a slow release of the OGFR antagonist.

In a further embodiment, the carrier is a bovine collagen implant. An OGFR antagonist, e.g., naloxone or naltrexone or a functional derivative thereof, can be combined with a bovine collagen implant, in a manner similar to either INFUSE (BMP2) or OP1-putty or OP1-implant, that is supplied with a bovine collagen sponge, powdered bovine collagen, or collagen based gelatin construct. Administration of naloxone, naltrexone or a functional derivative thereof can be achieved by, e.g., reconstituting the powdered naloxone or naltrexone or a functional derivative thereof with sterile saline and then adding the OGFR antagonist-saline solution to the collagen implant; after which the implant can be delivered locally to the site of surgical intervention.

In still another embodiment, the carrier is a surgical implant, or a surgical implant delivery system selected from e.g., cages, screws, rods, plates, expandable cages, anchors (metal based, synthetic or biodegradable anchors).

In a further embodiment, the carrier is composed of beta tricalcium phosphate in the form of chips or powers, cement (polymethylmethacrylate or "PMMA"), or a demineralized bone matrix scaffold in the forms of e.g., putty, paste, boats, or injectable formulations.

In another embodiment, the carrier is a carrier composed of PGA (poly glycolic acid)-PLGA (polylactic glycolic acid) spheres, which can encapsulate an OGFR antagonist to provide for immediate, delayed or sustained release.

In another embodiment, the carrier is an allograft such as corticocancellous allograpft, cortical chips and structural allograft.

In another aspect, this disclosure provides a method for promoting the recruitment of mesenchymal stem cells (MSC) to a local site of injury or surgical intervention in bone to promote healing while inhibiting osteoclast driven bone degradation (or re-absorption). The method is based on administration of an amount of an OGFR antagonist described herein (e.g., naloxone or naltrexone or a functional derivative thereof) to promote bone formation while inhibiting bone degradation.

In still another aspect, this disclosure provides a method of treating osteonecrosis or osteoradionecrosis based on administration of an OGFR antagonist described herein (e.g., naloxone or naltrexone or a functional derivative thereof).

In some embodiments, this disclosure provides a suitable dose range, through which naloxone (400-ng/mL (1-μM) to 400-μg/mL (1-mM)) and/or naltrexone (378-ng/mL (1-μM) to 378-μg/mL (1-mM)) is administered at doses that range between 1-μM and 1-mM and are effective to increase bone formation and/or decrease bone degradation through decreased osteoclast formation. Specific dose amounts of naloxone can be, for example, 400-ng/mL, 800-ng/mL, 1-μg/mL, 10-μg/mL, 50-μg/mL, 100-μg/mL, 400-μg/mL or an amount between any of the listed doses so long as these doses range between 1-μM and 1-mM. These dosage amounts can be delivered in a single administration or multiple administrations. The precise, total amount of naloxone that is effective will depend on the extent of the injury or surgical application and the carrier to be used. For example, 400-μg/mL naloxone-saline solution, or any equivalent dose, that is equal to 400-μg/cm$^3$ naloxone-saline solution, would be recommended for every collagen implant with dimensions 2-cm×2-cm×0.25-cm or 1-cm$^3$ of naloxone (e.g., collagen infused with 1-mM of a naloxone-saline solution) or a functional derivative thereof, which can be administered to an injury or local surgical site that results in substantial bone formation and inhibition of osteoclast numbers within the surgical area. Specific dose amounts of naltrexone can be, for example, 378-ng/mL, 756-ng/mL, 1-μg/mL, 10-μg/mL, 50-μg/mL, 100-μg/mL, 378-μg/mL or an amount between any of the listed doses. The precise, total amount of naltrexone that is effective will depend on the extent of the injury or surgical application and the carrier to be used. For example, 378-μg/mL naltrexone-saline solution, or any equivalent dose, that is equal to 378-μg/cm$^3$ naltrexone-saline solution, would be required for every collagen implant with dimensions 2-cm×2-cm×0.25-cm or 1-cm$^3$ of naltrexone (e.g., collagen infused with 1-mM of a naltrexone-saline solution) or a functional derivative thereof, which can be administered to an injury or local surgical site that results in substantial bone formation and inhibition of osteoclast numbers within the surgical area.

The present description is further illustrated by the following examples, which should not be construed as limiting in any way. The contents of all cited references (including literature references, issued patents, and published patent applications as cited throughout this application) are hereby expressly incorporated by reference.

Example 1: Opioid Antagonists Regulate Bone Formation and Re-Absorption

Methods:

Human bone marrow was collected from consenting adult patients undergoing either an elective primary proximal femoral total hip arthroplasty or elective primary distal femoral total knee arthroplasty (n=6, mean age 65) as a part of an IRB approved study. Human MSC were derived from the adherent fraction of cells derived from each whole bone marrow aspirate collected, while the monocyte population was collected from the non-adherent fraction of the bone marrow. The monocyte fraction was enriched through subculture with 100-ng/mL recombinant human macrophage colony-stimulating factor (MCSF; Wyeth). In parallel experiments described below, the femurs from 3-week (n=10) and 16-week (n=20) old male mice were collected and then the bone marrow was flushed from the femur according to the following: A 21-gauge needle was inserted into the femoral intramedular canal after the removal of the proximal and distal ends of the femur. Media was then carefully passed through the proximal end of the femur, which forced the bone marrow to pass out of the bone. Finally, the bone marrow pellet was mechanically disassociated using an 18-gauge needle and then passed through a 70-μm mesh filter. These whole bone marrow aspirates were used to generate osteoclasts. Cells were maintained in Dulbecco's Modification of Eagle's Media (DMEM) containing 10% fetal calf serum (v/v) and 1% penicillin-streptomycin-glutamine (PSG; Cellgro, Mediatech). Recombinant human netrin-ligands (NTN1 and NTN4) were diluted in PBS (R&D Systems). The responsible IACUC committee approved all of the animal studies described in this work.

Gene Expression Analysis:

MSC, osteoblasts and adipocytes derived from human bone marrow were assayed for changes in gene expression. In parallel, osteoclasts derived from human monocytes were also assayed for changes in myeloid gene expression. Gene data were derived from two independently generated samples collected from at least three patients. mRNA was purified using RNeasy Plus Mini columns (Qiagen) and cDNA was synthesized using the iScript cDNA Synthesis Kit (Bio-Rad). Gene expression was analyzed using quantitative PCR (qPCR) using 100-ng of cDNA mixed with Fast Plus EvaGreen Master Mix (Biotium). In each experiment GAPDH served as a control, negative controls contained no-template and a standard curve was generated using serial dilutions of a chemically synthesized sequence for GAPDH (0, 1, 10 and 100 femtograms; Integrated DNA Technologies). Gene expression was evaluated using Pfaffl's method, in which the efficiency of each primer (E) and the starting gene product concentration ($N_0$) are calculated from the linear region of the fluorescence-crossing threshold curve using the software LinRegPCR (v2013.0). Experiments were considered valid when the control gene GAPDH fell within the standard curve and the primer efficiencies (E) were calculated to be E>=1.8. The presence of a single gene product was confirmed using a melt-curve analysis and product size was confirmed using gene product gel-electrophoresis.

Protein Expression Through Western Blot Analysis:

Human MSC, osteoblasts and osteoclasts were lysed with cold RIPA buffer (Pierce Thermo Scientific) containing 2-mM iodoacetamide, 2-mM benzamidine hydrochloride, 0.1-mM ethylmaleimide, 1% PMSF and the Halt Protease Inhibitor Cocktail (Pierce Thermo Scientific). Protein lysates were analyzed from at least two replicates generated from three patient samples. Total protein was assayed using the BCA Protein Assay Kit (Thermo) following the manufacturers instructions. Samples were loaded (20-μg/well) onto a 10-20% Mini-Protean Tris-Tricine Precast Gel (Bio-Rad) with the Page Ruler Pre-stained NIR Protein Ladder (Bio-Rad) and transferred to a nitrocellulose membrane (Bio-Rad). OGFR was identified on membranes blocked using 5% non-fat milk with a OGFR primary antibody (Santa Cruz Biotechnologies). Actin (1:500) and δ-tubulin served as loading controls. Antibodies were detected using an HRP-conjugated micro-polymer conjugated secondary antibody (ImmPress kit, Vector Labs) in conjunction with the Clarity Western ECL substrate (Bio-Rad). Mouse brain protein lysates (mB) were used as positive-expression controls.

Osteogenesis:

Osteogenic potential in MSC was assayed by chemically inducing mineral formation. MSC from at least three human patients were seeded at $5 \times 10^3$ cells per well and allowed to become confluent and woven prior to the addition of osteo-induction media. Induction media consisted of DMEM containing 20% FCS (v/v) and 1% PSG supplemented with 25-μg/mL of acscorbic-2-phosphate (Sigma), 100-nM dexamethasone (Sigma) and the following dosing regimen of β-glycerophosphate (BGP; Sigma): 1× media change with 5-mM BGP, 1× media change with 10-mM BGP and 1× media change with 20-mM of BGP. Met5-ligand (0-, [5-μM] 2.87-, or [50-μM] 28.7-μg; Sigma), naloxone (0-, 400-fg, 400-μg, 400-ng, 400-μg; Sigma) or naltrexone (0-, 378-fg, 378-μg, 378-ng, 378-μg; Sigma) was added as follows: 1) 1×, with the first addition of osteo-induction media, 2) 2×, with the first and second addition of osteo-induction media and 3) with each post-induction media change. Positive control wells were treated with 25-ng of the recombinant human BMP2/BMP7-ligand (R&D Systems) with the first addition of induction media. After the appearance of mineral nodules, cells were fixed with 70% ice-cold EtOH (Sigma) and then stained using 40-mM alizarin red-S (pH 4.2, Sigma). Osteogenesis experiments were repeated at least twice for each patient.

Assay of Cell Number:

Following the addition of 1-mM naloxone or 1-mM naltrexone, viable cell number was determined with the MTT assay. After 72-hours and 120-hours, MTT (5 mg/ml (w/v), Sigma) was added to each well, incubated for 2-hours, after which the cells lysed with 500-μl of DMSO (Sigma). MTT was measured at 570-nm and the effects of therapy on cell proliferation were determined by normalizing treated wells relative to mean values from non-treated wells: Fold change in cell number=100*[treated cells optical density/mean control optical density].

TRAP Staining and the Assay of Osteoclast Number:

Osteoclasts were derived from either an enriched population of human monocytes or from mouse non-enriched whole bone marrow aspirates. Three human patient bone marrow samples were assayed in parallel with samples collected from 3-week (n=10) mouse bone marrow. The monocyte fraction was stimulated to become osteoclasts by culturing $1 \times 10^6$ cells with 25-ng/mL of MCSF and 25-ng/mL of recombinant human or mouse RANK-ligand (R&D Systems) in the presence of the met5-ligand ([5-μM] 2.87-, or [50-μM] 28.7-μg; Sigma), naloxone (400-ng or 400-μg; Sigma) or naltrexone (378-ng or 378-μg; Sigma). Osteoclasts were stained with tartrate resistant acid phosphatase (TRAP; Sigma Leukocyte Acid Phosphatase Kit 387-A) and counted when cells stained TRAP-positive and had at least three nuclei. Estimates of osteoclast number were obtained by Cavalieri sampling and a modification of the fractionator technique.

shRNA Knock-Down of the OGF-Receptor:

OGF-receptor activity was inhibited by transfecting MSC using a commercially available neogenin shRNA-lentivirus, or with a GFP lentivirus as a control (Santa Cruz Biotechnologies). MSC were then induced to become osteoblasts and subsequently assayed for BMP-target genes (ID1, ID2, SMAD1, SMAD2, SMAD3, SMAD4, SMAD5, SMAD6, SMAD7, SMAD8/9 and osteocalcin (OCN)).

Unicortical Defect Model:

Male 3-week old C57BL/6 mice (n=5 per treatment group) were injected with met5, naloxone or naltrexone following the creation of a unicortical defect. Briefly, a small incision (approximately 3-mm) was made just below the knee joint, located on the medial side of the tibia just below the tibial tuberosity on the tibial crest. In young animals the physeal plate is clearly visible and the drill bit was placed approximately 1-mm below this point. The drill-bit produces a unicortical defect with dimensions 300-μm diameter×1-mm depth. A Hamilton Neuros RN 10-μL syringe with a 33-gauge blunt tip needle was used to inject 2-μL of met5 (28.7-μg), naloxone (400-μg) or naltrexone (378-μg) resuspended in saline directly into the unicortical defect at a rate no faster than approximately 0.1-μL per second. The left-limb tibias served as contra-lateral surgical controls, in which animals received a unicortical defect and 2-μL of saline was injected. Mice were euthanized 5-days after surgery, hind limbs were collected and tibias were fixed for immunofluorescense, TRAP staining and OTC associated bone growth.

Implantation of Opioid Antagonist Containing Collagen Implant into a Unicortical Defect Model:

Male 5-week old C57BL/6 mice (n=5 per treatment group for a total of 25 total animals) were used in this study. Treatment groups consisted of the following: 1) PBS+ collagen sponge; 2) met5+collagen sponge; 3) BMP2+collagen sponge; 4) naltrexone+collagen sponge; 5) naloxone+ collagen sponge. Unicortical defects were surgically administered through a small incision (approximately 3-mm) made just below the knee joint, located on the medial side of the tibia just below the tibial tuberosity on the tibial crest. In 5-weeks old male mice, the physeal plate is clearly visible and the drill bit was placed approximately 1-mm below this point. The drill-bit produces a unicortical defect with dimensions 300-μm diameter×1-mm depth. Bovine collagen sponge implants (Duraform) were prepared (approximately 1-mm×1-mm) and then soaked in PBS, 50-μM (28.7-μg in 10-μL), met-5 enkephalin (met5), 25-ng BMP2, 1-mM naltrexone (378-μg in 10-μL) or naloxone 1-mM (400-μg in 10-μL) (n=5 for each group, 25 total animals). A unicortical defect was administered to a separate group of mice (n=5; Surgical Controls for cortical defect) that did not receive a collagen sponge implant. In parallel, a separate group of animals served as non-surgical controls. Mice were euthanized 7-days after surgery, hind limbs were collected and tibias were prepared for micro-CT (μCT) analysis.

Rat Posterolateral Spinal Fusion of L5-L6 Vertebrae:

20 male, 1-month old skeletally mature Sprague-Dawley rats underwent bilateral lumbar posterolateral spinal fusion at the L5-L6 vertebrae. Treatment groups will consist of the following: 1) sham surgery control; 2) collagen sponge implant; 3) BMP2+collagen sponge implant; 4) naloxone+ collagen sponge implant. Under sterile conditions a 2-cm long posterior midline incision centered at L5-L6 vertebrae was made. A muscle-splitting approach was used, lateral to the facet joints, to expose the transverse processes of a particular vertebra. A high-speed 1-mm burr was used to decorticate the transverse processes of the L5-L6 vertebrae. Implants were prepared and implanted between the transverse processes bilaterally in the paraspinal muscle bed. Bovine collagen sponge implants will be prepared (approximately 1-cm×1-cm) and then soaked in PBS, 25-ng BMP2, 1-mM naloxone (400-μg in 10-μL). Animals were euthanized 2-months (n=5 rats per time point per treatment group for a total of n=20 rats) spines were collected and prepared for micro-CT (μCT) analysis.

MicroCT Analysis of Unicortical Defects:

High-resolution images of the tibia were acquired with a μCT imaging system (μCT40; Scanco Medical). Tibias were scanned at 45-keV with an isotropic voxel size of 12-μm. An analysis region was selected from axial sections to include the entire unicortical defect bounded by the endosteal cortical wall. The volume corrected bone volume (bone volume/total volume; Bv/Tv), trabecular number (TbN) and trabecular thickness (TbTh) were calculated using the Scanco software.

Statistical Analyses:

Prism statistical software (Graphpad) was used to analyze data. Means and standard deviations were calculated. Data were analyzed by 1-way ANOVA using the Holm-Sidak post-hoc correction for multiple comparisons with significance set at $p<0.05$.

Figures 1D, 1E, 1F:
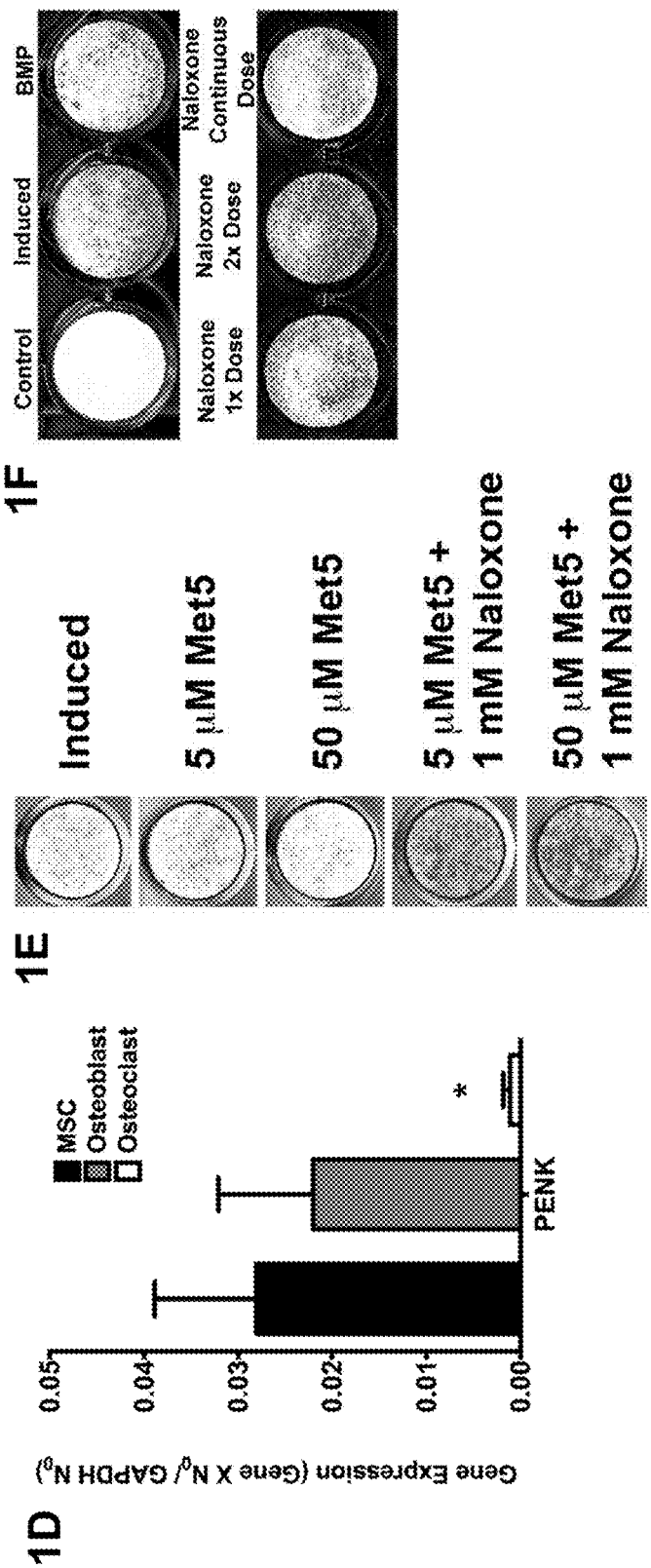
Figures 1G, 1H, 1I:
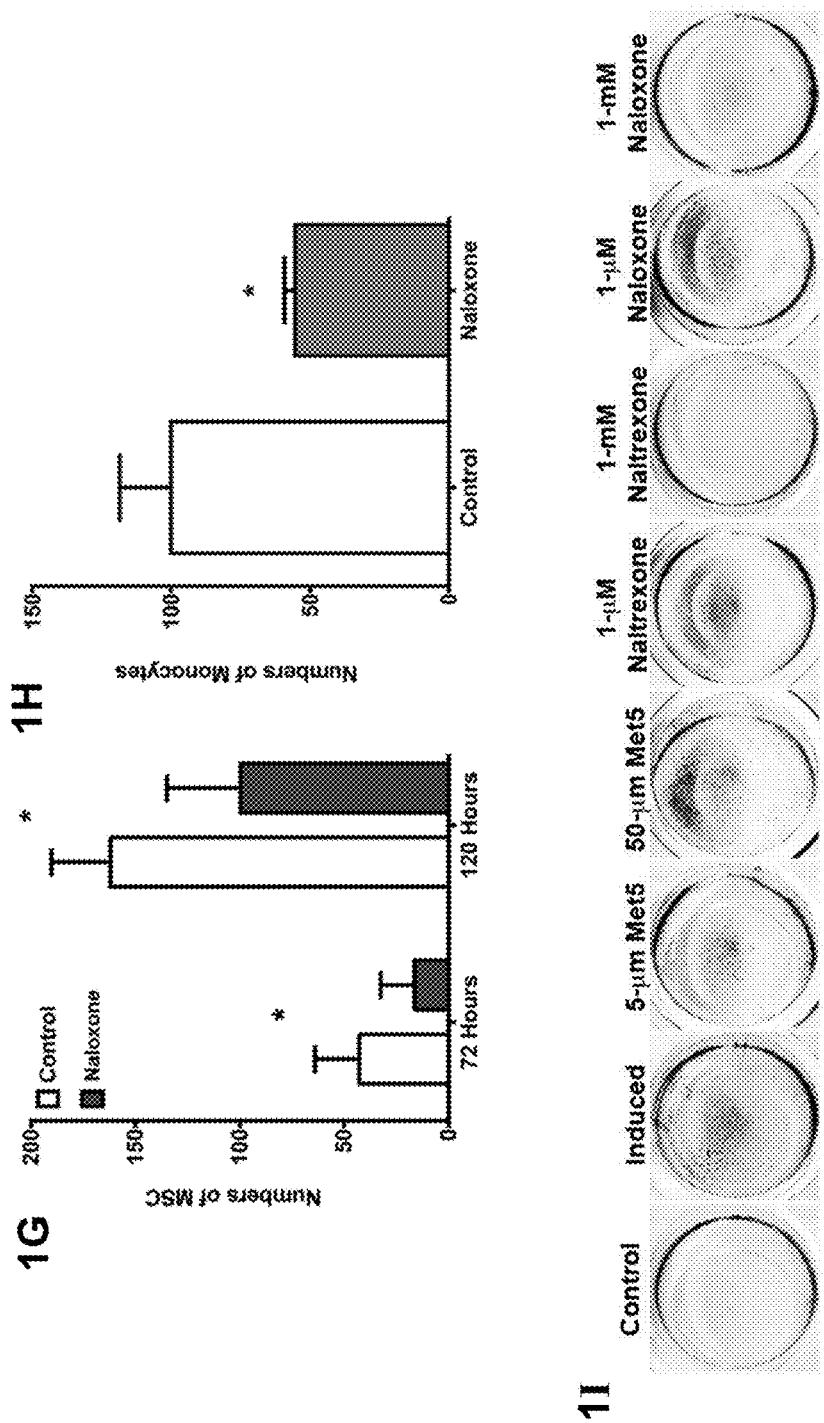

Results:

Naloxone and Naltrexone Increased MSC Differentiation into Osteoblasts and Mineral Formation while Decreasing Osteoclast Number:

The addition of naloxone between 1-μM and 1-mM with osteoinduction media substantially increased mineral accumulation (red staining) in MSC cultures induced to become osteoblasts (FIG. 1A). The addition of naltrexone between 1-μm and 1-mm with osteoinduction media also increased mineral, but to a lesser extent than naloxone (FIG. 1A). The delta opioid receptor (OPRD) gene expression was greatest in the MSC and significantly decreased in osteoblasts ($p<0.0074$) and osteoclasts ($p<0.0084$) (FIG. 1B). The OGFR gene expression was increased in osteoblasts ($p<0.011$) and osteoclasts ($p<0.0001$) relative to MSC cultures (FIG. 10). Met5 (PENK) gene expression was not different between MSC and osteoblasts; however, PENK gene expression was significantly decreased in osteoclasts ($p<0.0018$) (FIG. 1D). Adding 5-μM met5 (PENK) to osteoinduction media had no effect on mineral accumulation while 50-μm met5 decreased mineral accumulation slightly (FIG. 1E). However, when 1-mM of naloxone was added with 5-μM or 50-μM met5 and osteoinduction media, naloxone treatment was able to abrogate the anti-osteogenic effects of met5 (FIG. 1E). The μ-opioid receptor, the κ-opioid receptor, the met5 precursor POMC and the CPA1 enzyme gene expression were never observed. PCSK1, PCSK2, CPD and CPE gene expression were observed in MSC, osteoblasts and osteoclasts, but were not significantly different from one another. The addition of a single, 'pulse' dose of naloxone (1-mM) or a double, 'pulse' dose of naloxone (1-mM) 72-hours after the first 'pulse' dose resulted in a substantial increase in mineral accumulation while continuous naloxone dosing (e.g. with every media change) was slightly depressed (FIG. 1F). In addition, we found that the addition of 1-mM naloxone suppressed, but did not stop, MSC proliferation at 72-hours ($p<0.0177$) and 120-hours ($p<0.0001$) (FIG. 1G). Naloxone similarly decreased proliferation in monocyte cultures ($p<0.0001$) (FIG. 1H). Monocytes cultured to become osteoclasts were unaffected by treatment with met5 relative to control osteoclast cultures (TRAP staining is purple) (FIG. 1I). The addition of 1-μM of naloxone or 1-μM naltrexone did not significantly reduce osteoclast number while the addition of 1-mM of naloxone or 1-mM naltrexone reduced osteoclast number substantially (FIG. 1I).

The Loss of OGFR Expression Lead to Increased Expression of Osteogenic Transcriptional Regulators in Parallel with Increased Osteocalcin Expression.

MSC transfected with OGFR shRNA showed significantly reduced OGFR gene expression ($p<0.0085$) (FIG.

Figures 2A, 2B, 2C, 2D, 2E:
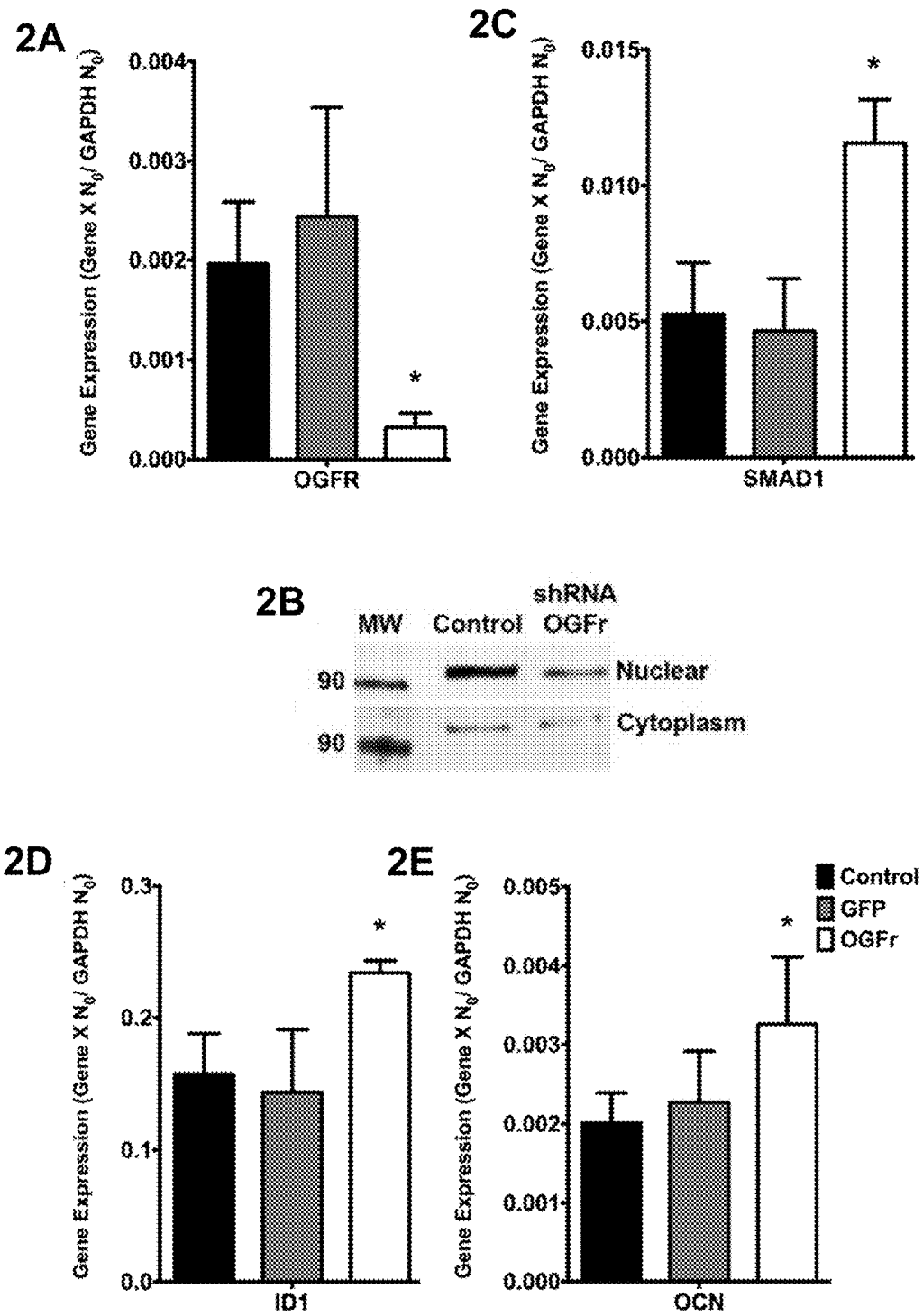
FIGS. 2A-2E: (A) MSC transfected with OGFR shRNA expressed significantly less OGFR gene expression (*=p<0.0085), which was corroborated (B) in decreased OGFR in nuclear and cytoplasmic protein lysates. (C) In addition, in OGFR deficient MSC SMAD1 gene expression was significantly greater than in control MSC and GFP transfected control cultures (*=p<0.0008). (D) ID1 gene expression was also increased in the OGFR deficient MSC relative to the control MSC and GFP transfected control cultures (*=p<0.0217). (E) The osteoblast specific protein osteocalcin (OCN) was also significantly increased in the OGFR deficient MSC induced to become osteoblasts relative to control cultures and GFP transfected control (*=p<0.0215).

2A), which was corroborated in decreased OGFR in nuclear and cytoplasmic protein lysates (FIG. 2B). In addition, in OGFR deficient MSC, SMAD1 gene expression was significantly greater than in control MSC and GFP transfected control cultures (p<0.0008) (FIG. 2C). ID1 gene expression was also increased in the OGFR deficient MSC relative to the control MSC and GFP transfected control cultures (p<0.0217) (FIG. 2D). The osteoblast specific protein osteocalcin (OCN) was also significantly increased in the OGFR deficient MSC induced to become osteoblasts relative to control cultures and GFP transfected control (p<0.0215) (FIG. 2E).

Treatment with Naloxone or Naltrexone Increased Bone Formation in Surgical Defect in an Animal Model.

Figures 3A, 3B, 3C:
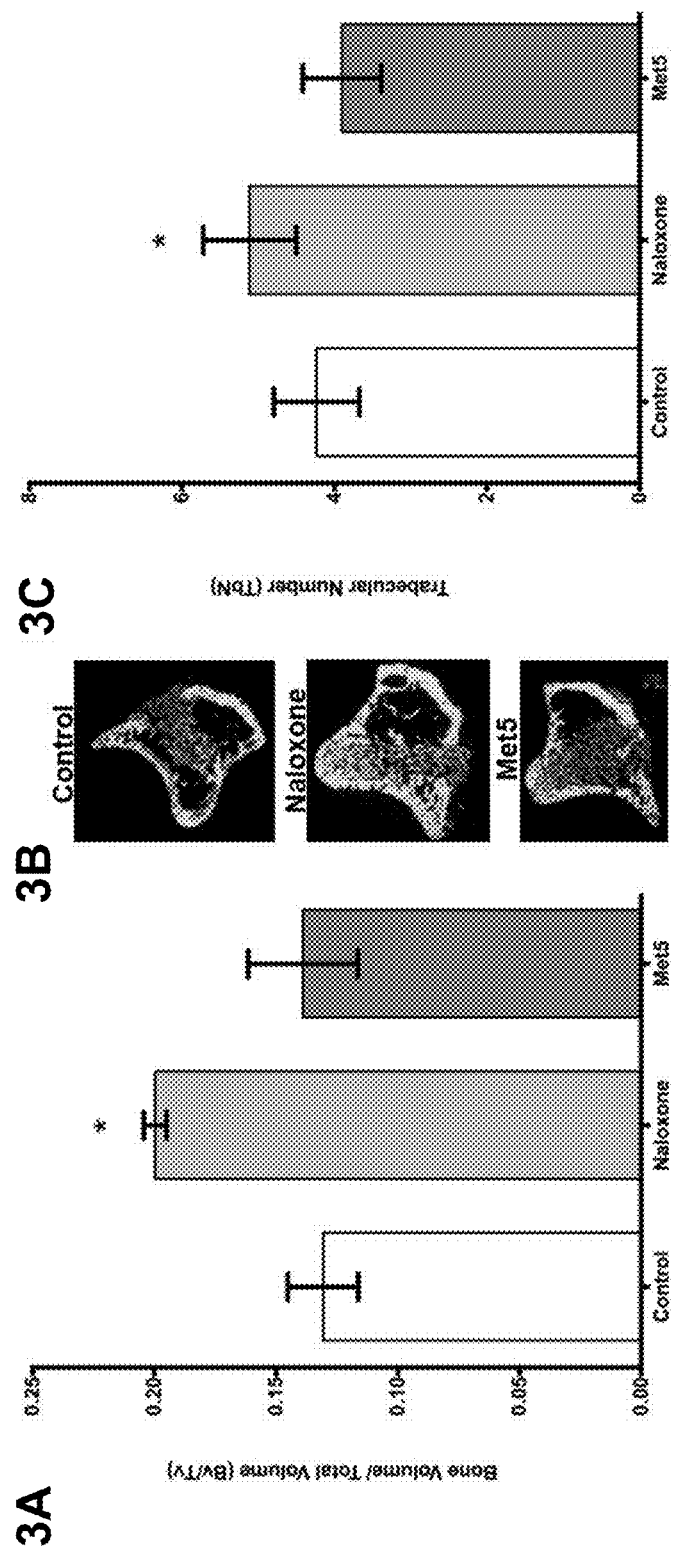
FIGS. 3A-3G: (A) The addition of 1-mM of naloxone treatment increased bone mass (Bv/Tv) 1.53-fold (*=p<0.001) in the unicortical defects relative to control PBS or met5 treated defects. (B) µCT images of the control, naloxone, or met5 treated group defects. (C) Elevated bone mass (Bv/Tv) paralleled a 1.2-fold increase in trabecular number (TbN) (*=p<0.047). (D) The surgical administration of a unicortical defect in the surgical control group (Sx Control) increased the Bv/Tv (bone volume corrected by total volume) relative to the control non-surgical group, which corresponds to bone mass that has accumulated within the defect (*=p<0.034). Defects treated with a bovine collagen implant and PBS or met5 were not different from surgical controls. However, both the PBS (*=p<0.0021) and the met5 (*=p<0.0009) treatment groups were significantly increased relative to the non-surgical control group. Defects treated with BMP2, naltrexone or naloxone were all increased relative to non-surgical controls (*=p<0.0001). The BMP2, naltrexone, and naloxone treatment groups were significantly increased when compared to the surgical control group (X=p<0.0005), the PBS treatment group (#=p<0.0124) and the met5 treatment group (+=p<0.011). The BMP2 treatment group By/Tv was not different from the naltrexone treatment group while the naloxone treatment group By/Tv was significantly increased (0=p<0.035). (E) Trabecular thickness (TbTh) was increased in the surgical control (Sx Control) group, the met5 treatment group, the BMP2 treatment group, the naltrexone treatment group and the naloxone treatment group (*=p<0.04). Only the TbTh in the naloxone treatment group was greater than the BMP2 treatment group or the naltrexone treatment group (**=p<0.0002). (F) The collagen implant increased bone formation in the lumbar spine relative to the SHAM surgery controls. However, the BMP2+collagen or the naloxone+collagen implant increased bone formation over the collagen implants alone. (G) µCT images of the lumbar bone fusion mass for the collagen implant and the naloxone+collagen implant.
Figures 3D, 3E:
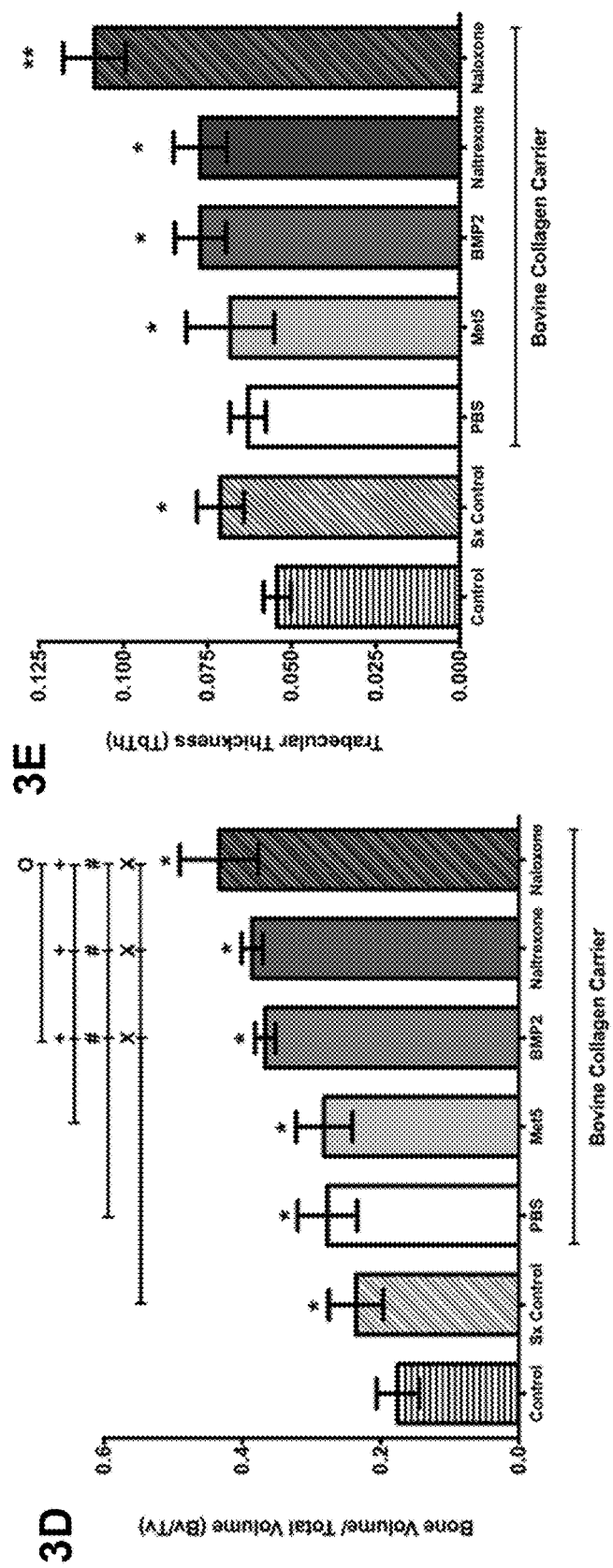
Figures 3F, 3G:
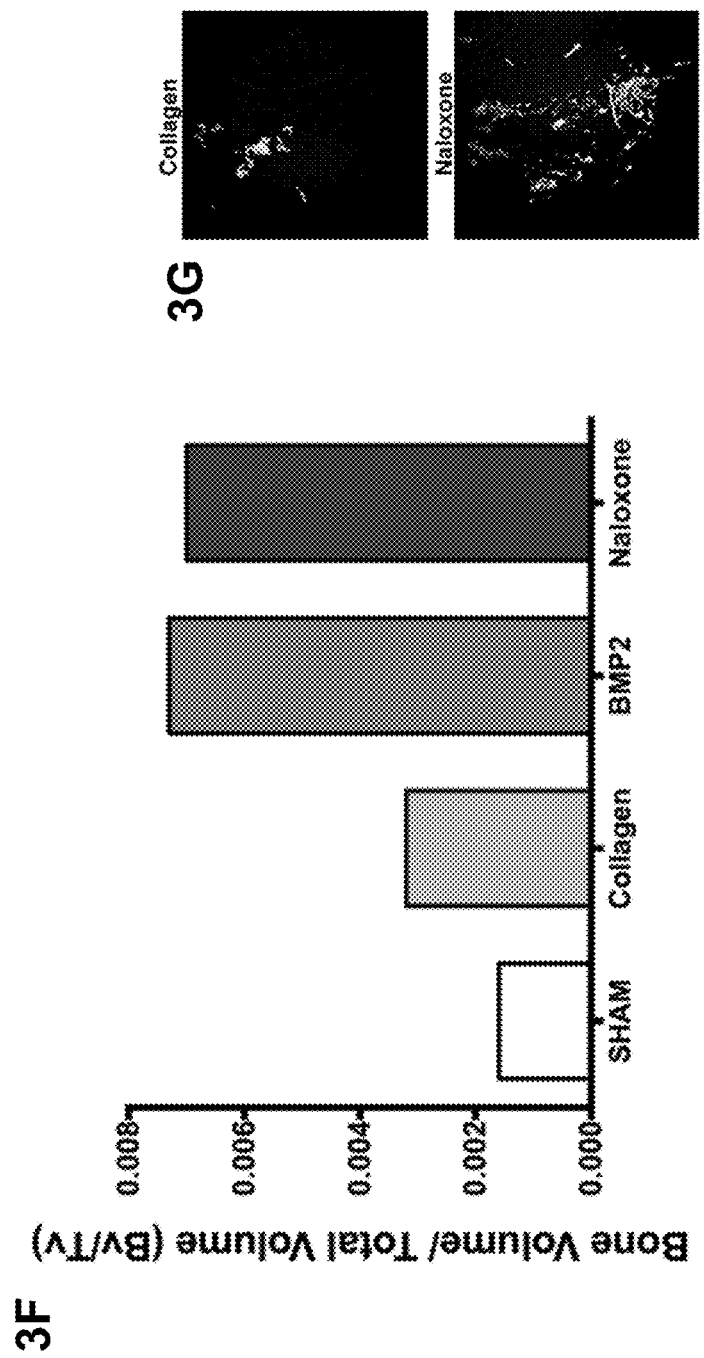

Unicortical defects were surgically administered to mouse tibias that were then treated with naloxone (1-mM) or met5 (50-μM). Naloxone increased bone healing while met5 had no effect (FIGS. 3A and 3B). Naloxone treatment increased bone mass (Bv/Tv) 1.53-fold (p<0.001) (FIG. 3A). The elevated bone mass that we measured was driven by a 1.2-fold increase in trabecular number (TbN) (p<0.047) (FIG. 3C). Seven days after the surgical administration, fracture healing of a unicortical defect as measured by By/Tv, was increased 25.6% in the surgical control group (Sx Control) relative to the non-surgical controls (p<0.034) (FIG. 3D). Defects treated with PBS or met5 in combination with a collagen implant were not significantly different from the surgical control group, with respect to fracture healing. However, the PBS or met5 treatment coupled with the collagen implant resulted in approximately 37% greater than the non-surgical control group, consistent with the difference observed between the surgical control and the non-surgical control groups (p<0.003) (FIG. 3D). Treating the defect with BMP2 and the collagen implant resulted in increased By/Tv 32.4% relative to the PBS treated group and 55.6% relative to the surgical control group (p<0.0124 and p<0.005, respectively) (FIG. 3D). There was no significant difference between the BMP2 treated group and the naltrexone treated group. The defects treated with naltrexone and a collagen implant increased By/Tv 39.2% relative to the PBS treatment group and 63.5% relative to the surgical control group (p<0.0043 and p<0.0001, respectively) (FIG. 3D). Finally, the defects treated with naloxone and the collagen implant had an increased By/Tv of 56.5% relative to the PBS treated defects and 83.8% relative to the surgical control group (p<0.0001) (FIG. 3D). Further, naloxone treatment increased By/Tv in the defect 18.2% relative to BMP2 treatment group (p<0.035) (FIG. 3D). Trabecular thickness is a structural parameter that relates to Bv/Tv, which relates to bone mass within the field of interest. The trabecular thickness was increased within the defect significantly in the surgical control (p<0.032), the met5 (p<0.039), the BMP2 (p<0.025), the naltrexone (p<0.025) and the naloxone (p<0.001) groups relative to the control non-surgical group (FIG. 3E). Treating the defect with naloxone increased trabecular thickness approximately 37% relative to all other treatment groups (p<0.001) (FIG. 3E). Also, the increase in By/Tv observed with naloxone treatment of the defects appears to be driven mostly through increased trabecular thickness while treatment with BMP2 or naltrexone increased By/Tv through both trabecular number and trabecular thickness. The addition of naloxone infused collagen implant to posterolateral lumbar spine resulted in a substantial increase in By/Tv relative to spines implanted with collagen or the control sham surgery group (FIGS. 3F and 3G).

Example 2: The OGFR Antagonists do not Stimulate Sarcoma Tumor Proliferation Despite OGFR Gene Expression in Sarcoma Cells Methods:

Human bone marrow was collected from consenting adult patients undergoing either an elective primary proximal femoral total hip arthroplasty or elective primary distal femoral total knee arthroplasty (n=6, mean age 65) as a part of an IRB approved study. Human MSC were derived from the adherent fraction of whole bone marrow aspirates. Ewing's sarcoma tumor cells (RDES, Hs822 and Hs863) and SaOS2 osteosarcoma tumor cells were obtained from ATCC. Cells were maintained in Dulbecco's Modification of Eagle's Media (DMEM) containing 10% fetal calf serum (v/v) and 1% penicillin-streptomycin-glutamine (PSG; Cellgro, Mediatech).

Gene Expression Analysis:

MSC, osteoblasts and adipocytes derived from human bone marrow were assayed for changes in gene expression. In parallel, osteoclasts derived from human monocytes were also assayed for changes in myeloid gene expression. Gene data were derived from two independently generated samples collected from at least three patients. mRNA was purified using RNeasy Plus Mini columns (Qiagen) and cDNA was synthesized using the iScript cDNA Synthesis Kit (Bio-Rad). Gene expression was analyzed using quantitative PCR (qPCR) using 100-ng of cDNA mixed with Fast Plus EvaGreen Master Mix (Biotium). In each experiment GAPDH served as a control, negative controls contained no-template and a standard curve was generated using serial dilutions of a chemically synthesized sequence for GAPDH (0, 1, 10 and 100 femtograms; Integrated DNA Technologies). Gene expression was evaluated using Pfaffl's method, in which the efficiency of each primer (E) and the starting gene product concentration ($N_0$) are calculated from the linear region of the fluorescence-crossing threshold curve using the software LinRegPCR (v2013.0). Experiments were considered valid when the control gene GAPDH fell within the standard curve and the primer efficiencies (E) were calculated to be E>=1.8. The presence of a single gene product was confirmed using a melt-curve analysis and product size was confirmed using gene product gel-electrophoresis.

Assay of Cell Number:

Following the addition of 1-mM naloxone or 1-mM naltrexone, viable cell number was determined with the MTT assay. After 72-hours and 120-hours, MTT (5 mg/ml (w/v), Sigma) was added to each well, incubated for 2-hours, after which the cells lysed with 500-μl of DMSO (Sigma). MTT was measured at 570-nm and the effects of therapy on cell proliferation were determined by normalizing treated wells relative to mean values from non-treated wells: Fold change in cell number=100*[treated cells optical density/mean control optical density].

Statistical Analyses:

Prism statistical software (Graphpad) was used to analyze data. Means and standard deviations were calculated. Data were analyzed by 1-way or 2-way ANOVA using the Holm-Sidak post-hoc correction for multiple comparisons with significance set at p<0.05.

Results:

Osteosarcoma and Ewing's Sarcoma Tumors Express the OGFR and Naloxone and Naltrexone Inhibit Tumor Proliferation.

Figure 4A:
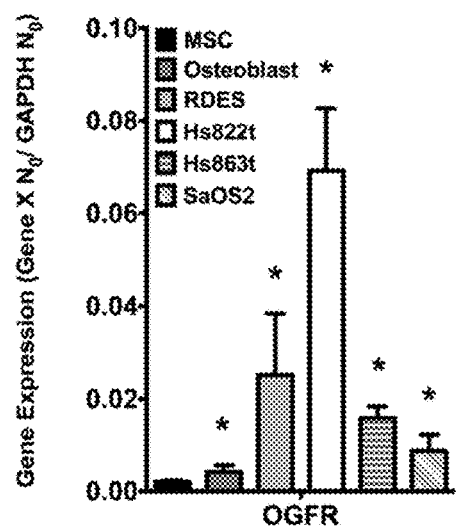
FIGS. 4A-4D: (A) OGFR gene expression was observed in osteoblasts (*=p<0.018), RDES Ewing's sarcoma of bone tumor cells (*=p<0.0014), Hs822t Ewing's sarcoma of bone tumor cells (*=p<0.0001), Hs863t Ewing's sarcoma of bone tumor cells (*=p<0.039) and SaOS2 osteosarcoma tumor cells (*=p<0.05). (B) Seventy-two hours after the addition of either 1-mM of naloxone or 1-mM of naltrexone, SaOS2 osteosarcoma cell number decreased significantly relative to the control cultures (*=p<0.0001). The OGFR ligand, met5, had not effect on cell number. (C) The Hs822t Ewing's sarcoma of bone tumor cell line are adherent in culture. Seventy-two hours after the addition of a 1-mM dose of naltrexone, Hs822t Ewing's sarcoma of bone tumor cell number decreased relative to the control cultures (*=p<0.0025). Naloxone had no effect of Hs822t tumor cell number. In contrast, the addition of 50-mM of met5 resulted in a significant increase in the number of Hs822t tumor cells (X=p<0.03). (D) The RDES Ewing's sarcoma of bone tumor cells are loosely adherent in culture. Seventy-two hours after the addition of either 1-mM of naloxone or 1-mM of naltrexone dose, RDES Ewing's sarcoma of bone tumor cell number decreased significantly relative to the control cultures (*=p<0.0005). The addition of met5 had no effect on RDES tumor cell number.
Figure 4B:
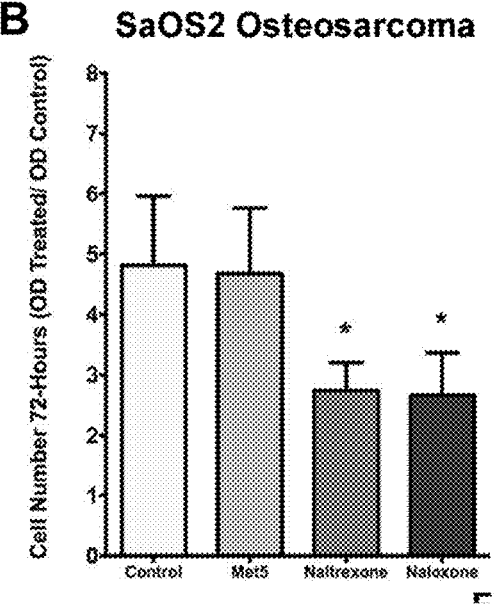
Figure 4C:
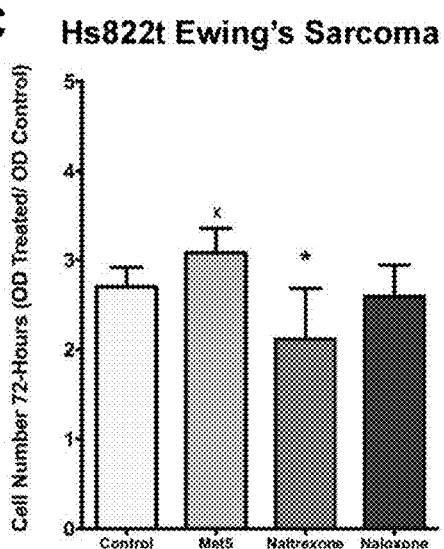
Figure 4D:
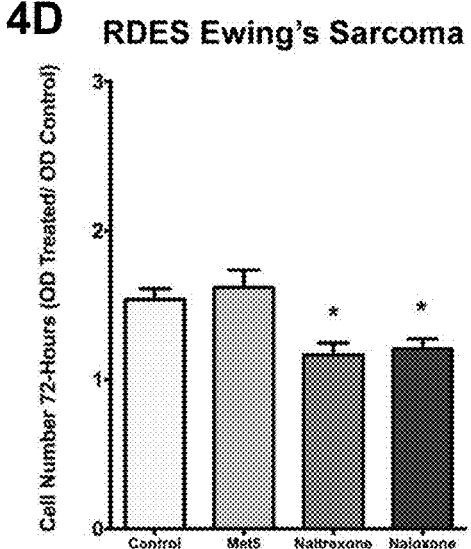

OGFR gene expression was observed in osteoblasts (p<0.018), RDES Ewing's sarcoma of bone tumor cells (p<0.0014), Hs822t Ewing's sarcoma of bone tumor cells (p<0.0001), Hs863t Ewing's sarcoma of bone tumor cells (p<0.039) and SaOS2 osteosarcoma tumor cells (p<0.05) (FIG. 4A). Seventy-two hours after the addition of either 1-mM of naloxone or 1-mM of naltrexone, SaOS2 osteosarcoma cell number decreased significantly relative to the control cultures (p<0.0001). The OGFR ligand, met5, had not effect on cell number (FIG. 4B). The Hs822t Ewing's sarcoma of bone tumor cell line are adherent in culture. Seventy-two hours after the addition of a 1-mM dose of naltrexone, Hs822t Ewing's sarcoma of bone tumor cell number decreased relative to the control cultures (p<0.0025). Naloxone had no effect of Hs822t tumor cell number. In contrast, the addition of 50-μM of met5 resulted in a significant increase in the number of Hs822t tumor cells (p<0.03) (FIG. 4C). The RDES Ewing's sarcoma of bone tumor cells are loosely adherent in culture. Seventy-two hours after the addition of either 1-mM of naloxone or 1-mM of naltrexone dose, RDES Ewing's sarcoma of bone tumor cell number decreased significantly relative to the control cultures (p<0.0005). The addition of met5 had no effect on RDES tumor cell number (FIG. 4D).

Summary of Results from Examples 1 and 2

Naloxone and naltrexone increase bone formation and reduce bone re-absorption (destruction) through a reduction in osteoclast number.

Naloxone or naltrexone infused collagen implants increased bone formation in a unicortical defect or fused lumbar vertebral bones.

Despite the presence of the OGFR, naloxone or naltrexone did not increase sarcoma tumor cell proliferation.

What is claimed is:

1. A method for promoting bone formation in a subject in need thereof, comprising locally administering an OGFR antagonist selected from the group consisting of naloxone, naltrexone, and a salt thereof to a site of injury or site of surgical intervention in the subject in an amount effective to promote bone formation at the site of injury or the site of surgical intervention in the subject, wherein the amount effective to promote bone formation is a locally administered dose of the OGFR antagonist between 1 μM and 1 mM.

2. The method of claim 1, wherein the OGFR antagonist is administered with a carrier.

3. The method of claim 2, wherein said carrier is a collagen based carrier in the form of a collagen sponge, a powdered collagen, or a collagen based gelatin hydrogel.

4. The method of claim 2, wherein the carrier is an albumin based carrier.

5. The method of claim 2, wherein the carrier is a hydrophilic hydrogel based carrier.

6. The method of claim 2, wherein the carrier is a surgical implant or a surgical implant delivery system.

7. The method of claim 2, wherein the carrier is composed of beta tricalcium phosphate, cement, or demineralized bone matrix.

8. The method of claim 2, wherein the carrier is composed of PGA/PLGA spheres.

9. The method of claim 1, wherein the OGFR antagonist is administered in combination with at least one other active agent to promote bone formation or growth.

10. The method of claim 1, wherein the injury comprises bone fracture.

11. The method of claim 1, wherein said surgical intervention is selected from a surgical repair of a fracture, a surgical procedure to create bone in spine fusion, and a surgical procedure to promote integration of orthopedic implants or hardware with adjacent bone.

12. The method of claim 1, wherein the OGFR antagonist is administered in a single administration.

13. The method of claim 1, wherein the OGFR antagonist naloxone or a salt thereof.

14. The method of claim 1, wherein the OGFR antagonist is naltrexone or a salt thereof.

* * * * *

UNITED STATES PATENT AND TRADEMARK OFFICE
CERTIFICATE OF CORRECTION

| | |
|---|---|
| PATENT NO. | : 10,208,306 B2 |
| APPLICATION NO. | : 14/723894 |
| DATED | : February 19, 2019 |
| INVENTOR(S) | : Nikhil A. Thakur and Bryan S. Margulies |

Page 1 of 1

It is certified that error appears in the above-identified patent and that said Letters Patent is hereby corrected as shown below:

On the Title Page

In the TITLE, and in the Specification Column 1, Lines 1-2, "COMPOSITIONS AND METHODS TO PROMOTE BONE FORMATION" should be -- COMPOSITIONS AND METHODS TO PROMOTE BONE FORMATION AND THEIR USES INCLUDING FOR THE TREATMENT OF CANCER --

Signed and Sealed this
Sixteenth Day of September, 2025

Coke Morgan Stewart
*Acting Director of the United States Patent and Trademark Office*

SEQUENCE LISTING

```
<160> NUMBER OF SEQ ID NOS: 5

<210> SEQ ID NO 1
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 1

Tyr Gly Gly Phe Met
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 2

Tyr Gly Gly Phe Leu
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa is N, N-diallyl-Tyrosine
<220> FEATURE:
<221> NAME/KEY: MISC_FEATURE
<222> LOCATION: (3)..(4)
<223> OTHER INFORMATION: Xaa is Aib (aminoisobutytic acid)
<220> FEATURE:
<221> NAME/KEY: L
<222> LOCATION: (6)..(6)
<223> OTHER INFORMATION: Leu is Leu-OH

<400> SEQUENCE: 3

Xaa Tyr Xaa Xaa Phe Leu
1               5

<210> SEQ ID NO 4
<211> LENGTH: 8
<212> TYPE: PRT
```

```
<213> ORGANISM: Artificial Sequence
<220> FEATURE:
<223> OTHER INFORMATION: Synthetic Peptide
<220> FEATURE:
<221> NAME/KEY: F
<222> LOCATION: (1)..(1)
<223> OTHER INFORMATION: Phe at position 1 is D-Phe
<220> FEATURE:
<221> NAME/KEY: MISC_FEATURE
<222> LOCATION: (7)..(7)
<223> OTHER INFORMATION: Xaa is Pen (Pencillamine)
<220> FEATURE:
<221> NAME/KEY: T
<222> LOCATION: (8)..(8)
<223> OTHER INFORMATION: Thr is Thr-NH2

<400> SEQUENCE: 4

Phe Cys Tyr Trp Lys Thr Xaa Thr
1               5

<210> SEQ ID NO 5
<211> LENGTH: 50
<212> TYPE: PRT
<213> ORGANISM: Artificial Sequence
<220> FEATURE:
<223> OTHER INFORMATION: Synthetic Peptide

<400> SEQUENCE: 5

Gln Ser Ala Leu Asp Tyr Phe Met Phe Ala Val Arg Cys Arg His Gln
1               5                   10                  15

Arg Arg Gln Leu Val His Phe Ala Trp Glu His Phe Arg Pro Arg Cys
            20                  25                  30

Lys Phe Val Trp Gly Pro Gln Asp Lys Leu Arg Arg Phe Lys Pro Ser
        35                  40                  45

Ser Leu
    50
```